(12) United States Patent
Nickson

(10) Patent No.: US 7,468,612 B2
(45) Date of Patent: *Dec. 23, 2008

(54) DERMAL PHASE METER WITH IMPROVED REPLACEABLE PROBE TIPS

(75) Inventor: Steven W Nickson, Derry, NH (US)

(73) Assignee: Nova Technology Corporation

( * ) Notice: Subject to any disclaimer, the term of this patent is extended or adjusted under 35 U.S.C. 154(b) by 62 days.

This patent is subject to a terminal disclaimer.

(21) Appl. No.: 11/306,686

(22) Filed: Jan. 6, 2006

(65) Prior Publication Data

US 2007/0222467 A1    Sep. 27, 2007

Related U.S. Application Data

(63) Continuation-in-part of application No. 10/908,327, filed on May 6, 2005, now Pat. No. 7,161,364.

(51) Int. Cl.
*G01R 31/02*    (2006.01)
*G01R 31/28*    (2006.01)

(52) U.S. Cl. ............... 324/761; 324/754; 324/158.1
(58) Field of Classification Search ............... 324/761
See application file for complete search history.

(56) References Cited

U.S. PATENT DOCUMENTS

| | | | |
|---|---|---|---|
| 3,929,018 A | 12/1975 | Turner | 73/343 |
| 5,297,055 A | 3/1994 | Johnstone | 364/474.37 |
| 5,413,107 A | 5/1995 | Oakley et al. | 128/662.06 |
| 5,479,930 A | 1/1996 | Gruner et al. | 128/662.06 |
| 5,522,826 A * | 6/1996 | Daily | 606/159 |
| 5,643,177 A * | 7/1997 | Ortiz et al. | 600/204 |
| 5,898,311 A * | 4/1999 | Bodenweber et al. | 324/754 |
| 5,961,471 A | 10/1999 | Nickson | 600/546 |
| 6,106,517 A | 8/2000 | Zupkas | 606/20 |
| 6,186,959 B1 | 2/2001 | Canfield et al. | 600/559 |
| 6,393,130 B1 | 5/2002 | Stonikas et al. | 381/322 |
| 6,408,981 B1 | 6/2002 | Smith et al. | 181/315 |
| 7,063,698 B2 * | 6/2006 | Whayne et al. | 606/49 |
| 7,161,364 B1 * | 1/2007 | Nickson | 324/754 |
| 2002/0107502 A1 | 8/2002 | Hung et al. | 604/506 |
| 2003/0171700 A1 | 9/2003 | Martin et al. | 601/2 |

* cited by examiner

*Primary Examiner*—Ha T. Nguyen
*Assistant Examiner*—Roberto Velez
(74) *Attorney, Agent, or Firm*—George A. Herbster

(57) ABSTRACT

A probe for a dermal phase meter includes a handle with a removable extension that terminates with a displaceable center conductor. A replaceable tip attaches to the distal end of the extension and includes a center conductor that engages the center conductor in the extension and an outer conductor that establishes electrical connection through the extension. Substituting different replacement tips provides a probe with an articulation capability.

4 Claims, 9 Drawing Sheets

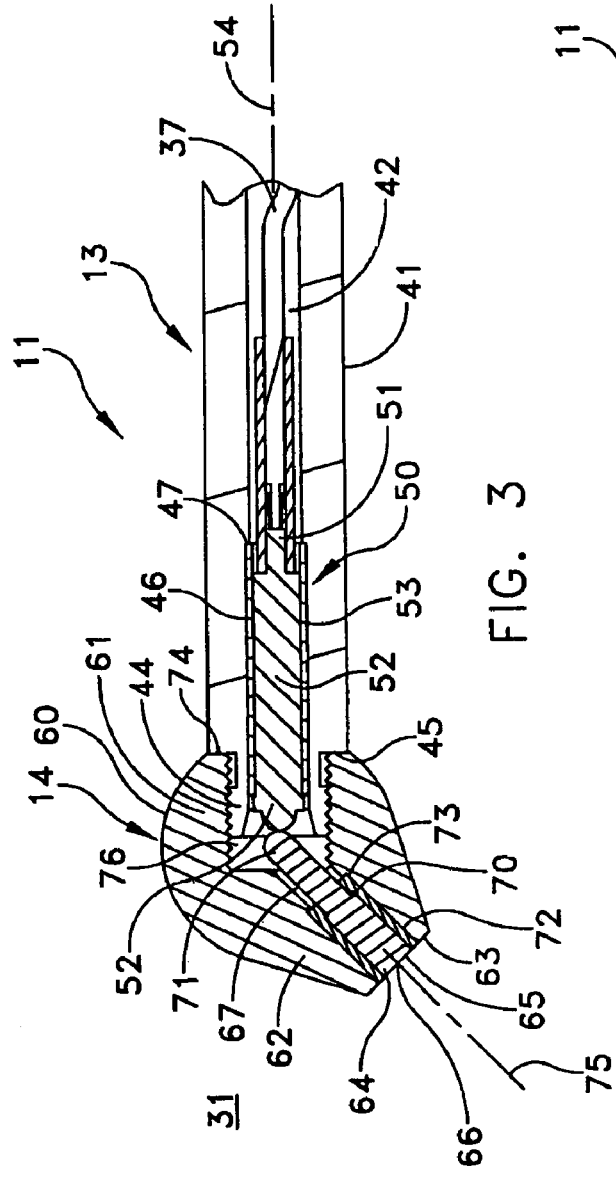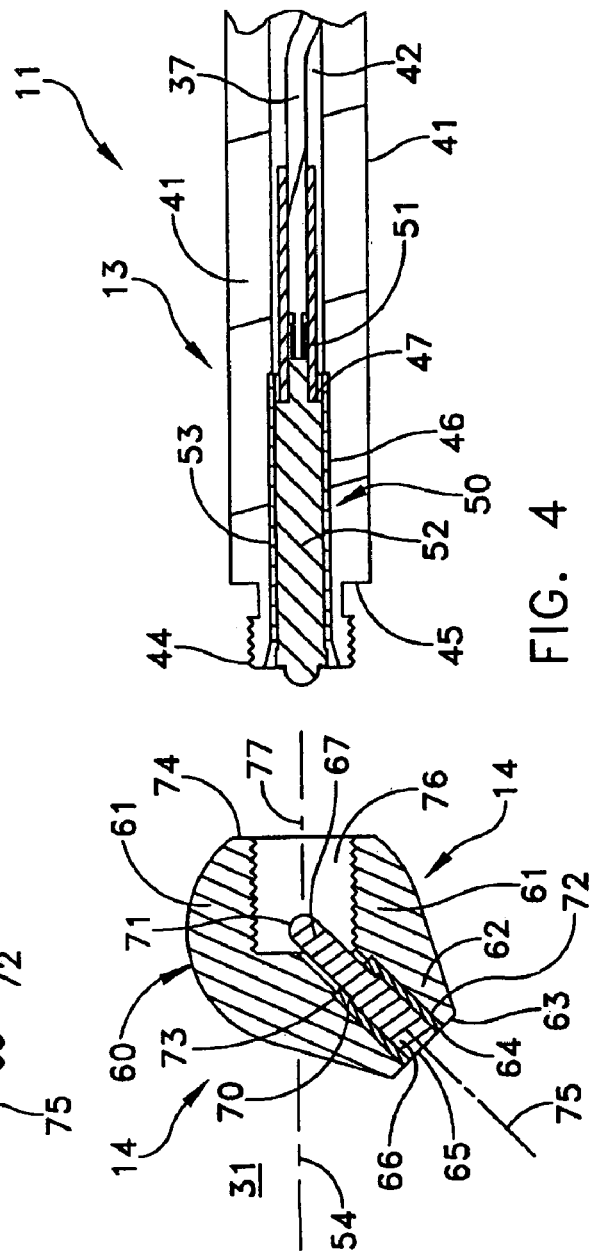

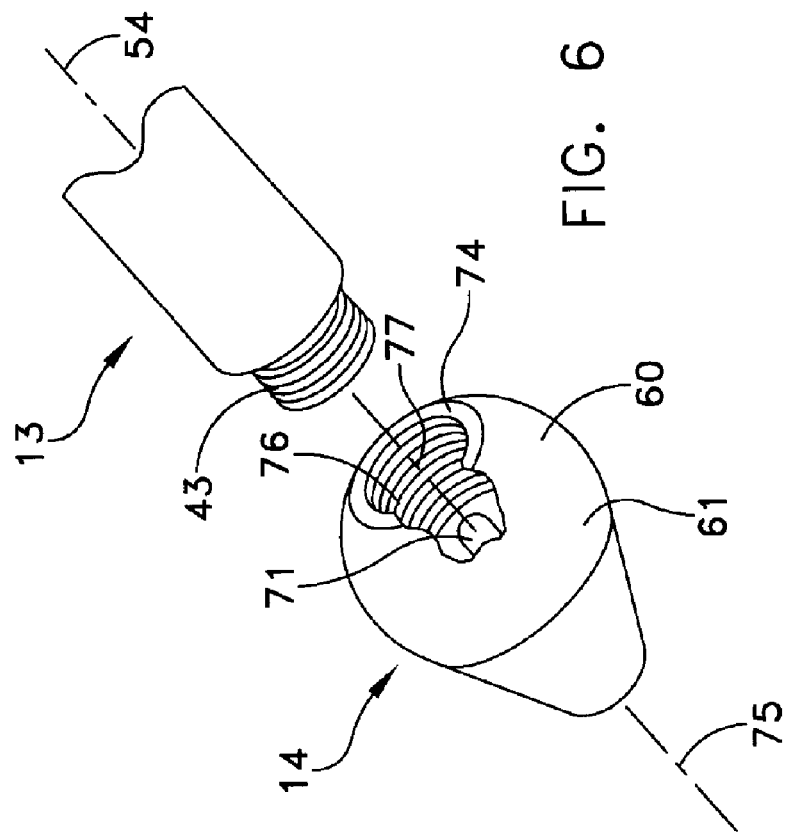
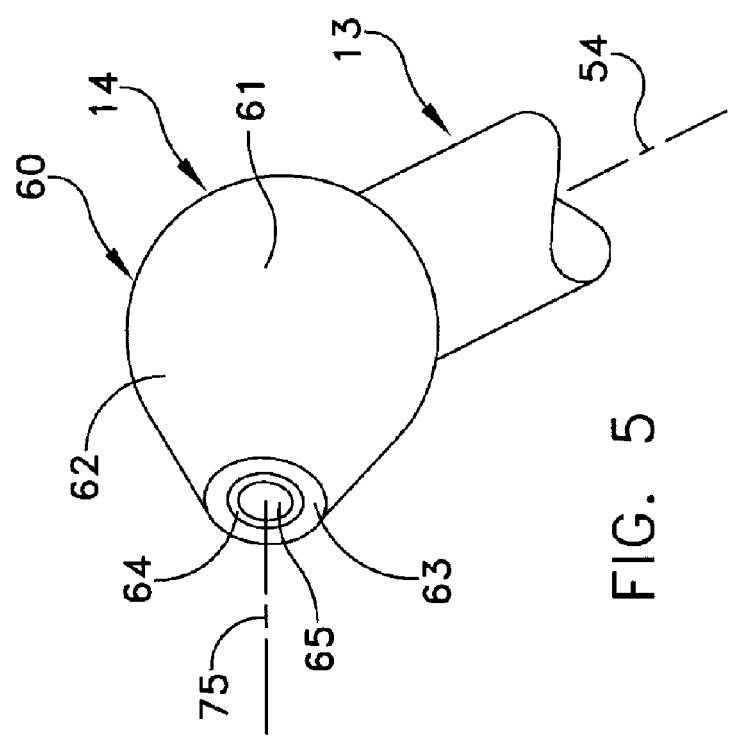

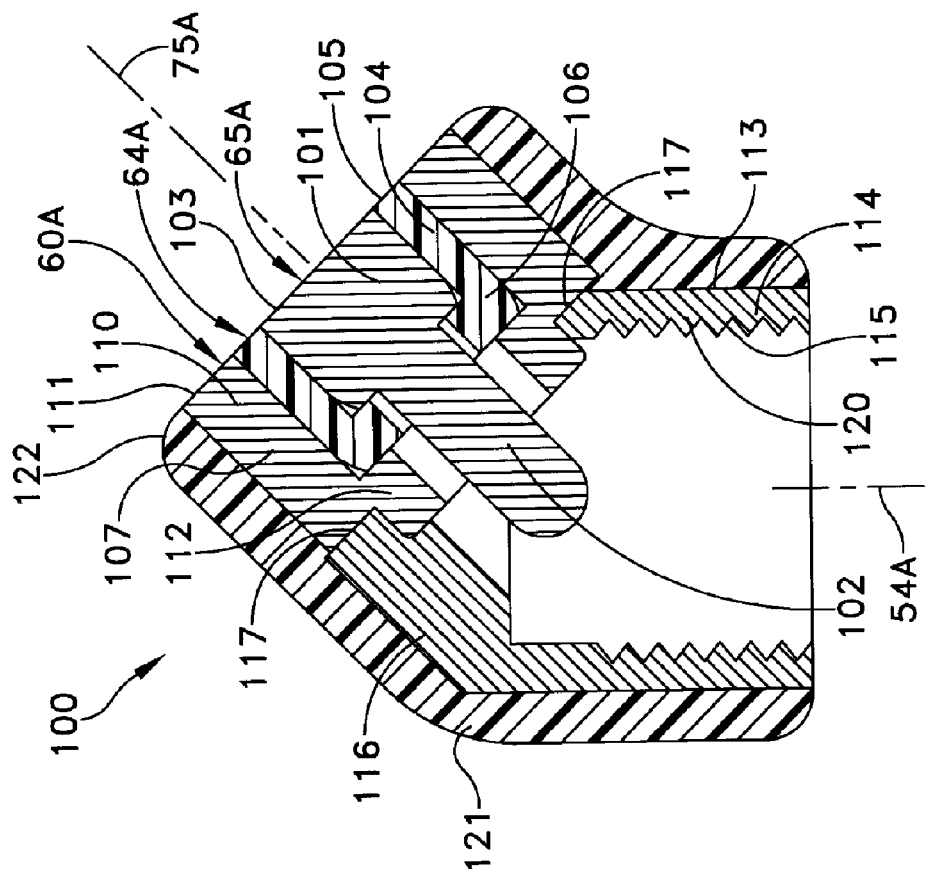
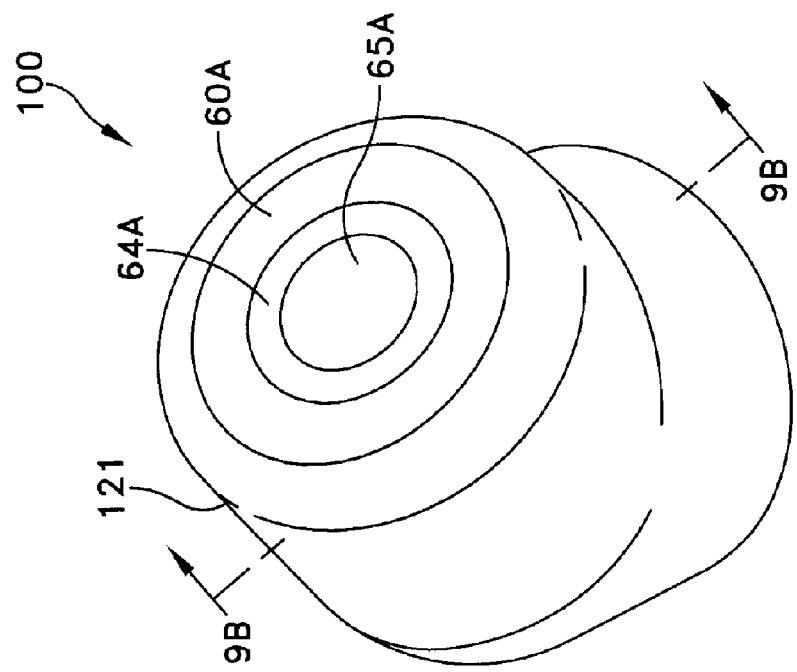

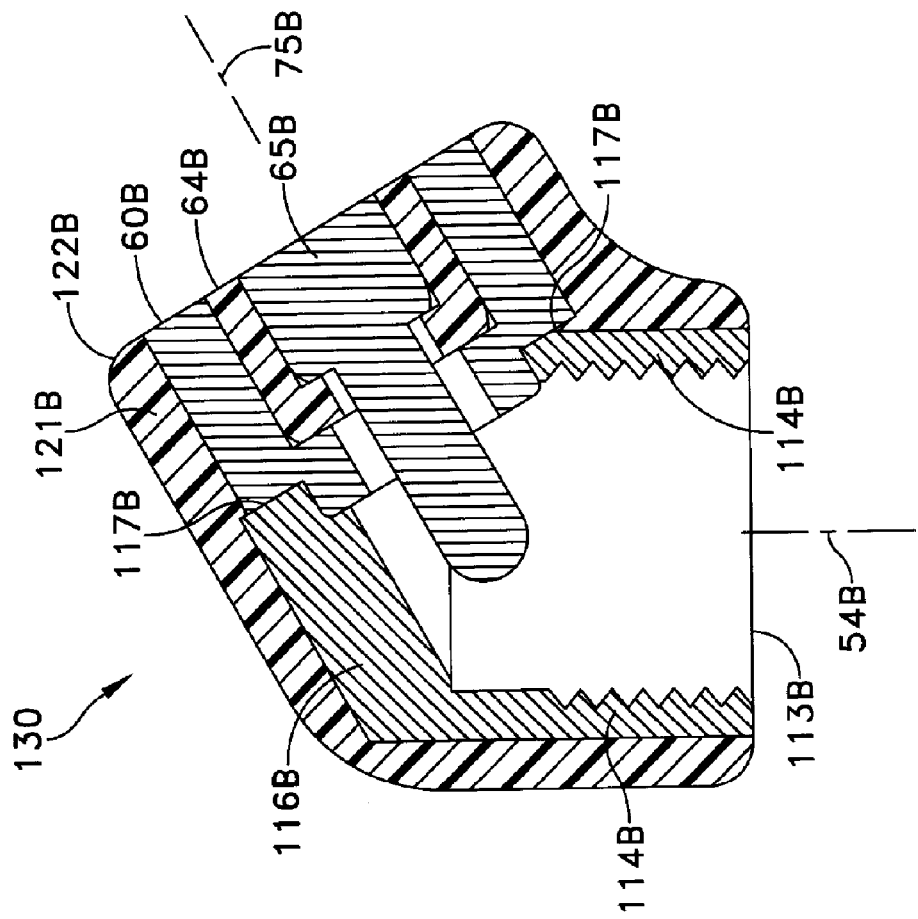
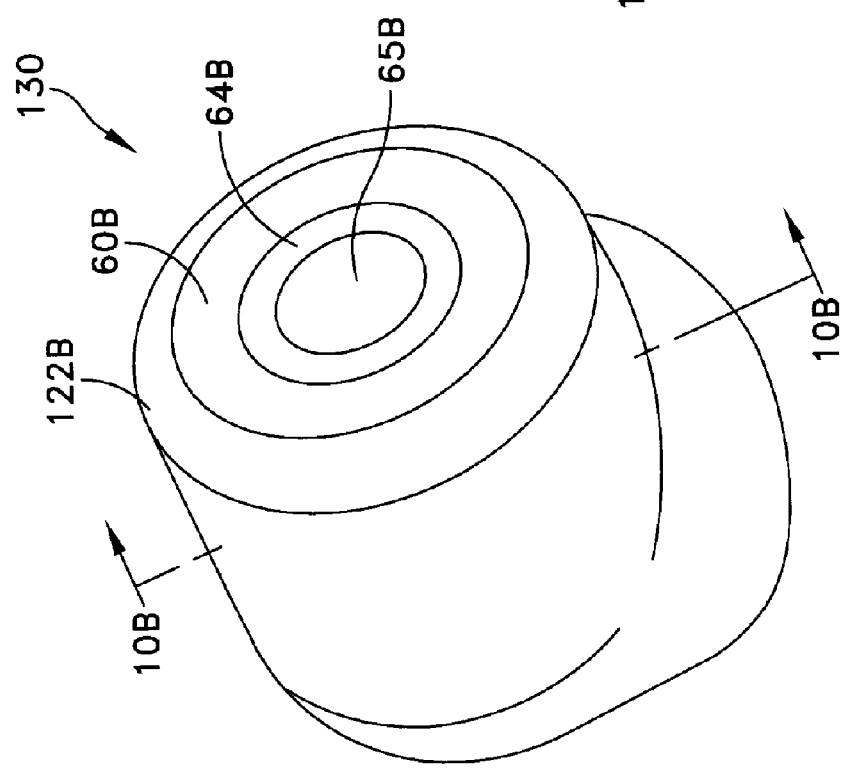
FIG. 10B
FIG. 10A

DERMAL PHASE METER WITH IMPROVED REPLACEABLE PROBE TIPS

CROSS REFERENCE TO RELATED APPLICATION

This application is a continuation-in-part of application for U.S. patent Ser. No. 10/908,327 filed May 6, 2005; now U.S. Pat. No. 7,161,364, for a Dermal Phase Meter with Replaceable Probe Tips.

FIELD OF THE INVENTION

This invention generally relates to dermal phase meters and more specifically to a probe that can broaden the applications for such dermal phase meters.

DESCRIPTION OF RELATED ART

Over the years there has been a growing interest in measuring the relative hydration of a substrate, such as the skin, for determining certain biophysical characteristics. U.S. Pat. Nos. 5,961,471 and 6,370,426 disclose different probes for obtaining such measurements. U.S. Pat. No. 5,961,471 to Nickson particularly discloses a probe for biophysical skin measurements that includes a disposable sensor and a handle for receiving a cable from a measurement device. A socket on the handle electrically interconnects with the cable. This disposable sensor removably engages the socket. When engaged, the sensor electrically interconnects with the cable for providing measurement signals concerning the biophysical skin measurement.

It now appears that measurements from such dermal phase meters may be used in models to indicate other medical conditions by applying a sensor to internal tissue, such as in the oral, anal, otic and nasal passages. Certain investigations are determining the efficacy of modeling the evaluation of oral mucositis by making measurements at multiple regions in the oral cavity for erythema and ulcerations. Other investigations are directed to determining the efficacy of such instruments in evaluating trauma, particularly hemorrhagic shock.

Probes, such as shown in the above-identified references, tend to be cumbersome and have a sensing surface that lies in a measurement plane that is orthogonal to a probe axis. To extend dermal phase meters to these new modalities, it has become important that the probes must be smaller. However, even smaller probes may be difficult to position within a cavity when the measurement plane is orthogonal to the probe axis. Probes characterized by a fully articulated measurement plane are complex and not particularly adapted to miniaturization. Moreover, many prior art probes terminate in solid, hard structures. Such structures can irritate sensitive tissue in these cavities.

What is needed is a probe that provides an articulation function, that is simple to use and that is economical to produce and that minimizes the potential for irritating sensitive tissue during measurements.

SUMMARY

Therefore it is an object of this invention to provide a probe that minimizes tissue irritation.

Another object of this invention is to provide a probe that is adapted for altering the aspect of the measurement plane to the probe axis that minimizes the potential for the irritation of sensitive tissue.

In accordance with one aspect of this invention a dermal phase meter system includes a data processing system and a probe for providing input to the data processing system. The probe comprises a set of probe tips, a probe tip support and an electromechanical connection. Each probe tip includes inner and outer electrodes spaced by an insulating medium lying in a measurement plane for obtaining a measurement. The probe tip support lies along a probe axis with means at a proximal end thereof for connection to the data processing system. The electromechanical connection has components on the distal end of the probe tip support and on each probe tip thereby to enable the electrical and mechanical attachment and detachment of a probe tip to the distal end of the probe tip support whereby each of the probe tips are characterized by establishing a different angular aspect between the probe axis and the measurement plane. At least one probe tip includes a patient compatible, compressible elastomeric layer about the outer electrode In accordance with another aspect of this invention a probe for a dermal phase meter comprises a handle, a tubular extension and a replaceable probe tip. The handle has an externally insulated conductive body and a proximal electrical connector supported thereby. The tubular extension has a central passage along a probe axis attached to a distal end of the body. The extension has a threaded connection and an axially displaceable spring biased conductor assembly in said passage. The replaceable probe tip has an outer conductive body and first and second passages lying on first and second intersecting axes, an insulator in said first passage and a conductor supported by said insulator extending into said second passage with an internally threaded portion extending along the second axis for attachment to and detachment from said threaded connection on said extension, said outer conductive body having a patient compatible, compressible elastomeric layer about said outer electrode.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which:

FIG. 3 is an enlarged detail of the distal end of the probe shown in FIG. 2;

FIG. 4 is an enlarged view corresponding to FIG. 3 with a probe tip separated from a probe handle;

FIG. 5 is a perspective view of a probe tip taken from the distal end of the probe in FIG. 1;

FIG. 6 is a perspective view of a probe tip taken from the proximal end;

FIG. 9A is a perspective view of one embodiment of a probe tip with a patient compatible, compressible elastomeric outer layer having a first aspect; and FIG. 9B is a cross section taken along lines 9B-9B in FIG. 9A;

FIG. 10A is a perspective view of one embodiment of a probe tip with a patient compatible, compressible elastomeric outer layer like the probe tip in FIG. 9A, but with another angular aspect; and FIG. 10B is a cross section taken along lines 10B-10B in FIG. 10A.

DESCRIPTION OF ILLUSTRATIVE EMBODIMENTS

Figure 1:
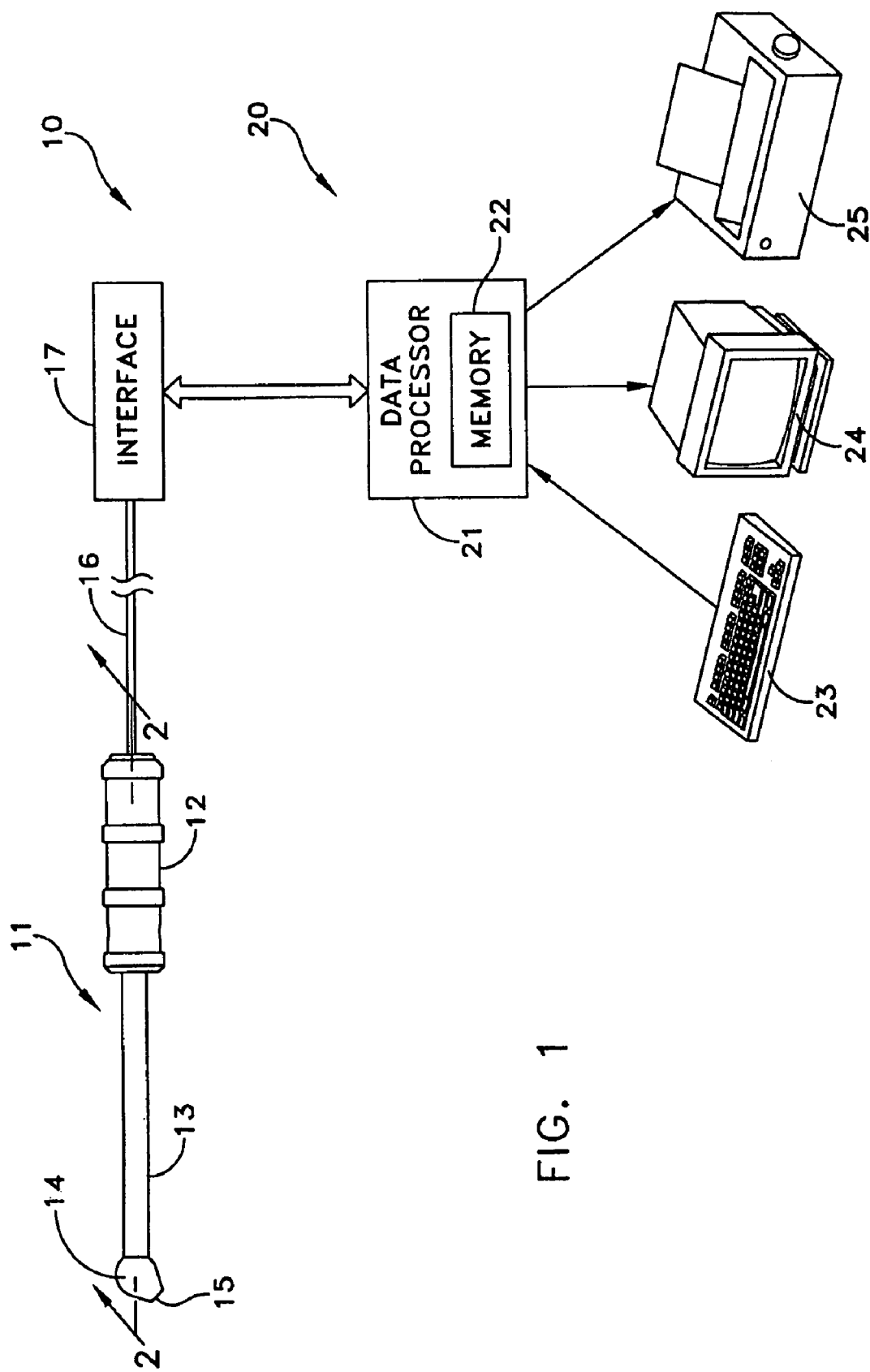
FIG. 1 schematically depicts a dermal phase meter with a probe having a given aspect between a probe axis and a measurement plane.

FIG. 1 depicts one embodiment of a dermal phase meter 10 that includes a probe 11. The probe 11 includes a probe tip support in the form of a handle 12 at a proximal end and an extension 13 intermediate the handle 12 and a distal probe tip 14. The distal tip 14 has measuring surface 15 that can have a variety of forms. Essentially the measuring surface 15 lies in a measurement plane defined by two electrodes spaced by an insulating medium.

Other conductors 16 couple the electrodes in the distal tip 14 to an interface 17 that includes various electronics for sampling data to read the signal developed across the electrodes at some sampling frequency. A data processing system 20 controls the operation of the probe 11 through the interface 17. The data processing system 20 includes a data processor 21 with a memory 22, an input device shown in the form of a keyboard 23, and one or more output devices, shown as a video display 24 and a hard copy printing device 25. As will be apparent the specific implementation of the data processing system 20 can take many forms that are well within the purview of persons of ordinary skill in the art.

Figure 2:
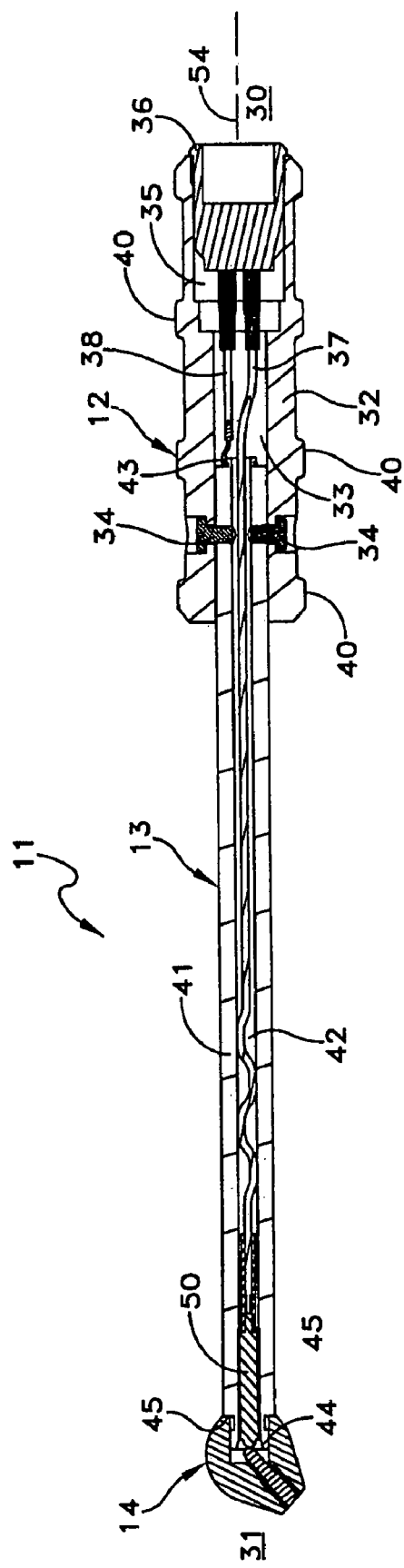
FIG. 2 is a longitudinal cross section of the probe shown in FIG. 1.

Referring now to FIG. 2, the probe 11 extends from a proximal end 30 at the handle 12 to a distal end 31 at the probe tip 14. The handle 12 has a generally cylindrical body 32 with a receptacle 33 to receive the extension 13. In this specific embodiment, a fastener attaches the cylindrical body 32 to the extension 13. As an example, in FIG. 2 diametrically opposed machine screws 34 extend radially through the cylindrical body 32 to engage the extension 13.

The proximal end of the handle 12 also has a proximally facing receptacle 35 that receives a proximal electrical connector 36. The connector 36 is adapted to receive a cable, such as the cable 16 shown in FIG. 1. The connector 36 also has two conductors 37 and 38. The conductor 37 is insulated and extends from the connector 36 through the extension 13 to the tip 14 as described below. The conductor 38 attaches to the extension 13 by soldering or other means.

The cylindrical body 32 is formed from an engineering polymer, such as Delrin®, with axially spaced, circumferential beads or bands 40. The beads or bands 40 form a gripping surface for the probe 11. The cylindrical body 32 thereby constitutes an insulated handle.

In this embodiment, the extension 13 is formed as a tube 41 with a central passage 42. Although not shown, the exterior surface of the tube 41 has an insulating coating so it acts as an externally insulated conductive extension. This allows the tube 41 to act as a conductor for the signals received from the tip 14 and be handled without electrical contact by personnel. A proximal radial surface 43 provides a connection point for the conductor 38.

Referring now to FIGS. 2 through 4, at the distal end 31, the tube 41 terminates in an externally threaded head portion 44 and radial shoulder 45. As shown more clearly in FIGS. 3 and 4, an enlarged, elongated chamber 46 in the tube 41 extends to an internal radial shoulder 47. This chamber 46 receives an axially displaceable spring biased conductor assembly 50, also shown in FIG. 2. Referring again to FIGS. 3 and 4, such assemblies are commercially available and comprise a proximal end connection 51 for the conductor 37, a center conductor 52 and an insulating housing 53. The assembly 50 includes an internal spring, not shown, that biases the center conductor 52 distally, along a probe axis 54. This structure provides a continuous conductive path between the center conductor 52 and the end connection 51 even as the center conductor 52 moves axially within the insulating housing 53. A P3325 Series Probe manufactured by Everett Charles Technologies is an example of such an assembly 50.

Still referring to FIGS. 3 and 4, a tip 14 constructed in accordance with this invention attaches to the extension 13 in FIG. 3 and detaches from the extension 13 in FIG. 4. As it will become apparent, each tip 14 constructed in accordance with this invention has certain, common characteristics and features. Referring to FIGS. 3 through 5, each tip 14 is formed from a solid bulbous conductive material, such as brass, to form an outer conductor 60 with a main enlarged bulbous body portion 61 and a conical portion 62 that tapers to a measuring surface 63. The tip 14 carries an insulator 64 and a central conductor 65 in a first passage extending along a measurement axis 75 orthogonal to the measuring surface 63 described later. The surface 63 formed by the ends of the outer conductor conical portion 62, insulator 64 and center conductor 65 defines the measurement plane thereby to provide a sensing surface by which a measurement is obtained. As with the tube 41, the surface of the outer conductor 60 will be coated with an insulating material.

The center conductor 65 has an enlarged shank portion 66 and a narrower portion 67 delimited by a shoulder 70. The end of the narrower shank 67 terminates in a semispherical conductor portion 71. The insulator 64, that is positioned in the conical section 62, overlies the larger shank portion 66 and has a cylindrical body 72 with a collar 73 that engages the shoulder 70. The reduced shank portion 67 including the semispherical tip 71 is isolated from the outer conductor 60. It will also be apparent that the center conductor 67 extends to intersect the probe axis 54.

The outer conductor 60 also includes a planar surface 74 that lies in a plane that is normal to another axis that, in FIGS. 3 and 4, is coincident with the probe axis 54. This first axis and probe axis 54 are angularly offset from the measurement axis 75 normal to the planar surface 63 at an angle β. More specifically, an internally threaded hole or passage 76 extends in the direction along an axis 77, as the first axis, that is perpendicular to the planar surface 74 and coincident with the probe axis 54. The angle β between the measurement axis 75 and the axis 77 defines the angular aspect of the measurement plane for the given probe tip 14. In this specific embodiment β=45°.

A complementary electromechanical connection provides a means for mounting a detached probe 14, as shown in FIG. 4 onto the distal end of the extension 13 as shown in FIG. 3. Specifically, it is merely necessary to screw the tip 14 onto the threaded head portion 44 as shown in FIG. 3 whereby the axis 77 and probe axis 84 are coincident. As rotation of the probe tip 14 relative to the extension 13 continues, the probe tip 14 advances proximally until the semispherical conductor portion 71 engages and makes electrical contact with the distal end of the center conductor 52 of the assembly 50. The structures will be dimensioned so that this contact occurs prior to engagement of a radial shoulder that defines the planar surface 74 and the shoulder 45. Further advancement and tightening of the probe tip 14 advances the probe tip 14 proximally and forces a displacement of the center conductor 52 against the bias of the internal spring of the assembly 50. A comparison of FIGS. 3 and 4 depicts this displacement. As a result the center conductor 52 and the center conductor 65 maintain good electrical contact. The outer conductor 60 has good electrical contact with the tube 40 by virtue of the threaded engagement.

Figure 7:
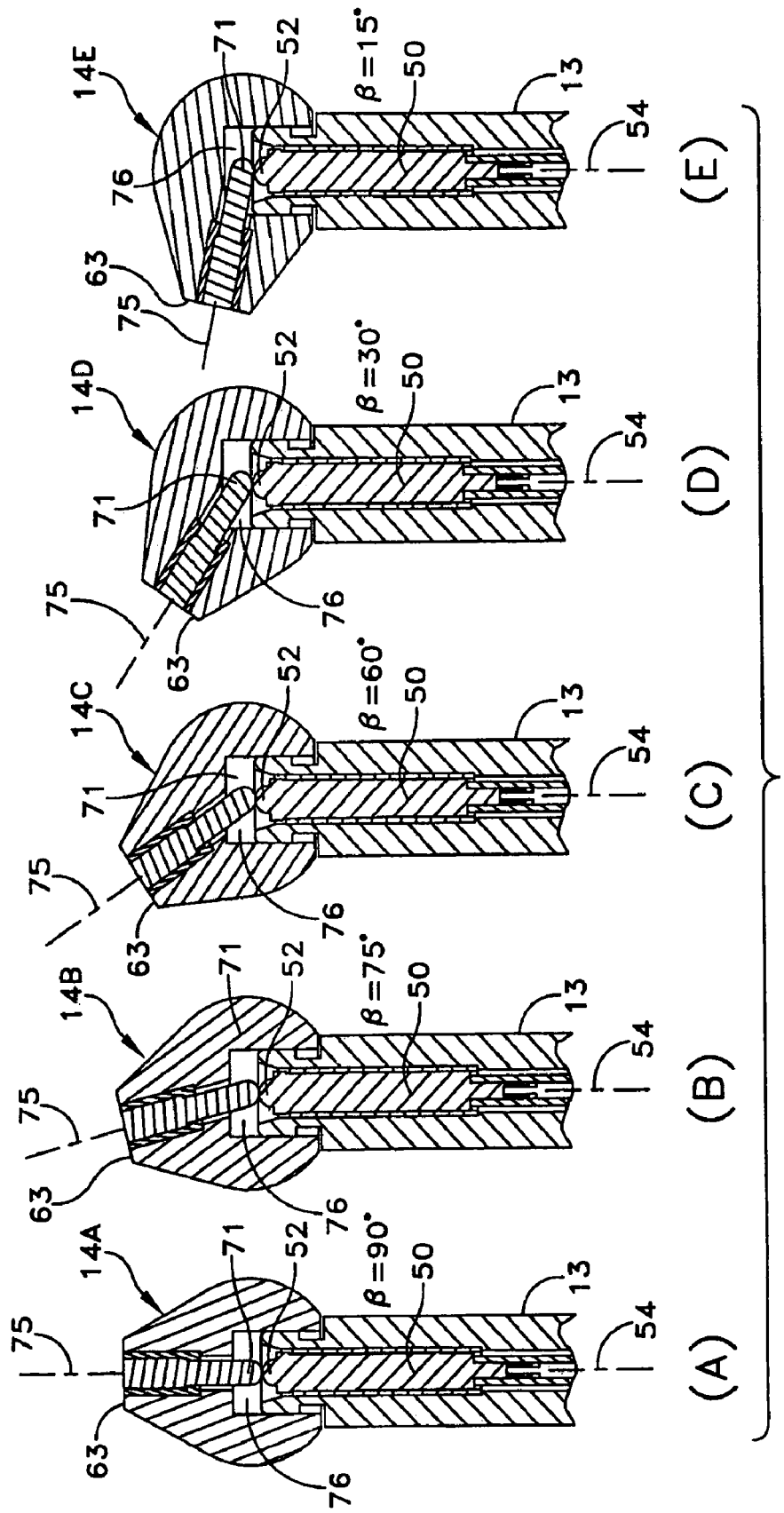
FIG. 7 depicts probe tips at (A) through (E) with different aspects between the measurement plane and probe axis.

To achieve the articulation function, a measurement system as shown in FIG. 1 can be constructed with a set of a plurality of probe tips 14 each of which provides a different angular aspect between the probe axis and the measurement plane. While FIGS. 2 through 6 depict a probe with an angular aspect of 45°, FIG. 7 depicts probes (A) through (E) with the measurement plane defined by the end 63 surface at different angular aspects. That is, each differs by the orientation of the probe axis 54 and coincident first axis (not shown in FIG. 7) and the measurement axis 75. For example, FIG. 7A depicts a probe tip 14A that provides a 90° aspect of the measurement plane defined by the surface 63 and the probe axis 54. In this particular case the hole 76 extends along the axis 75. Contact with the center conductor 52 is shown. At (B) in FIG. 7 a tip 14B in which the axis 75 through the hole 76 is offset to provide a 75° aspect. The probes at (C) through (E) depict distal tips 14C, 14D and 14E, which provide aspects of 60°, 30° and 15° respectively.

Any of the replaceable tips 14A through 14E on the extension 13 produces the necessary electrical connections to provide the appropriate readings. Moreover the 15° shifts of the aspect of the measurement plane relative to the probe axis 54 provide maximum flexibility in enabling contact with tissues in internal cavities that were not previously available. However, it will be apparent that these tips are easily manufactured and economical to produce and easy to use.

Figure 8:
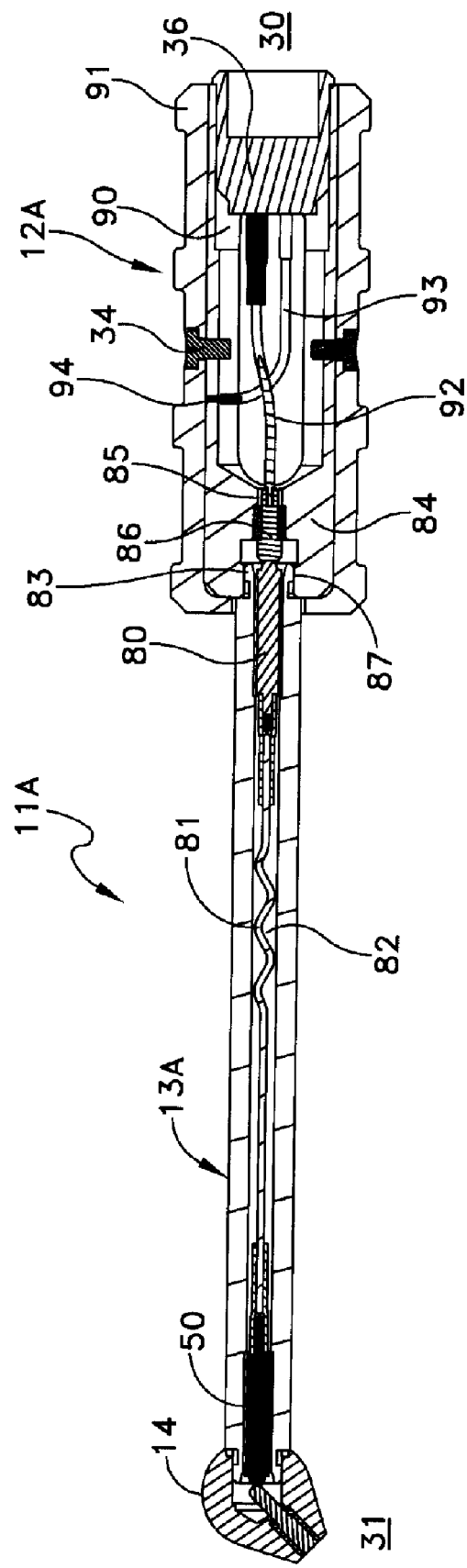
FIG. 8 depicts a longitudinal cross section of another embodiment of a probe.

The probe 11 shown in FIG. 2 provides replaceable probe tips 14 that can attach and detach from an extension 13 that is fixed in the handle 12. In some situations the examination process may contaminate the surface of the extension. Therefore it would be helpful if the extension were also replaceable. FIG. 8 depicts a modified probe 11A that achieves this objective. As many of the components in the probe 11A are similar to those in the probe 11 of FIGS. 2 through 4, like numerals are used to designate like elements. Modified elements are designated by different references numerals annotated with "A".

Referring to FIG. 8, the probe 11A has a replaceable distal tip 14 attached to the distal end 31 of the modified extension 13A. The modified extension 13A connects at its proximal end to a modified handle 12A. The interface between replaceable tips, such as the replaceable tip 14, with different aspects and the distal end of the extension in probe 11A is the same as shown with respect to the probe 11 in FIGS. 2 through 4. Consequently, no further discussion of this connection is necessary.

The modification to the extension 13A involves the termination at the proximal end. With this modification the proximal end of the extension 13A contains a spring biased conductor assembly 80, like the spring biased conductor assembly 50. A conductor 81 in a passage 82 connects the spring biased conductor assemblies 50 and 80. The modified extension 13A also terminates at a distal end with an externally threaded portion 83.

The handle 12A includes a central conductive body 84 with a central passage 85 that receives a fixed conductor 86. The distal end of the central conductive body 84 incorporates an internally threaded socket 87. With this configuration rotating the extension 13A relative to the handle 12A provides attachment or detachment of the extension 13A and the handle 12A. The interaction of the spring biased conductor assembly 80 and the conductor 86 provides the necessary signal path to the connector 36 located in a proximal receptacle 90. The modified extension 13A therefore is an independent structure or subassembly that can be handled separately from both the replaceable probe tip 14 and the handle 12A.

The handle 12A additionally includes an insulating cover 91 overlying the central conductive body 84. Machine screws 34 coated of a plastic material affix the insulating cover to the central conductive body 84. A conductor 92 provides a signal connection to the conductor 86. A ground connector 93 extends from the connector 36 to a ground connection 94 formed with the central conductive body 84. Thus the conductive path established between the body of the distal tip 14, the body of the modified extension 13A and the central conductive body 84 is coupled back through the connector 36 to complete the sensing circuit.

As will now be apparent, this construction does provide the advantage of allowing modified extensions 13A to be removed and replaced easily at a diagnostic facility. Consequently it is more readily adapted for use in a medical facility. It may also be possible to apply the concept by implementing modified extensions 13A and handles 12A where the extensions 13A have different lengths. However, such a modification will require calibration of the dermal phase meter of FIG. 1 because changes in the length of the modified extension 13A can alter the electrical characteristics of the probe 11A.

FIGS. 9A through 11B depict three alternative embodiments of a probe tip construction that minimizes the potential for irritating sensitive tissue in a body cavity during a diagnosis. This particular probe is optimized for diagnosing ear problems by inserting the probe into the otic canal.

Figure 11B:
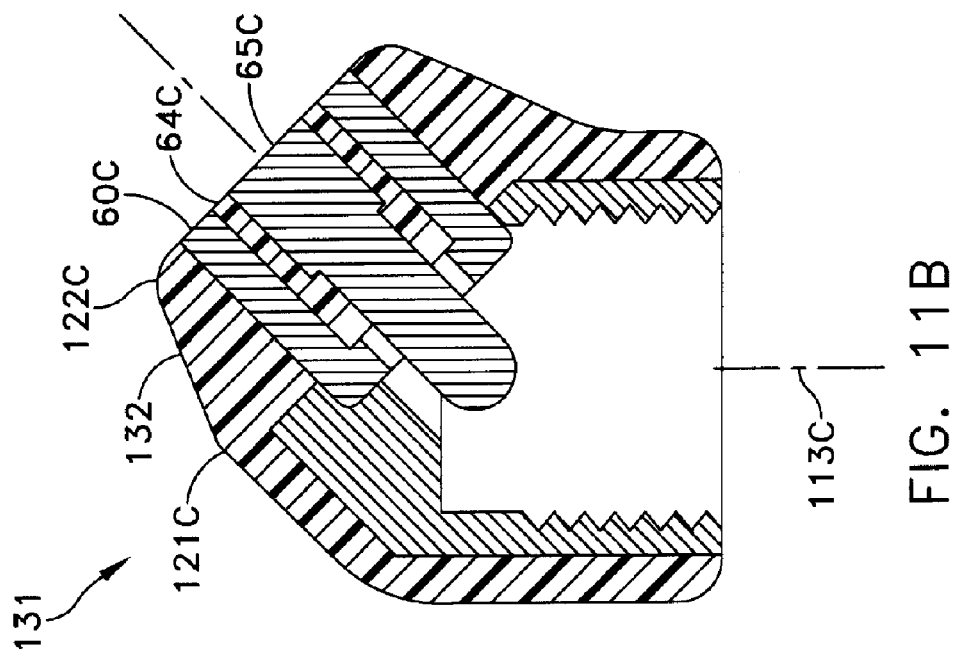
FIG. 11B is a cross section taken along lines 11B-11B in FIG. 11A.
Figure 11A:
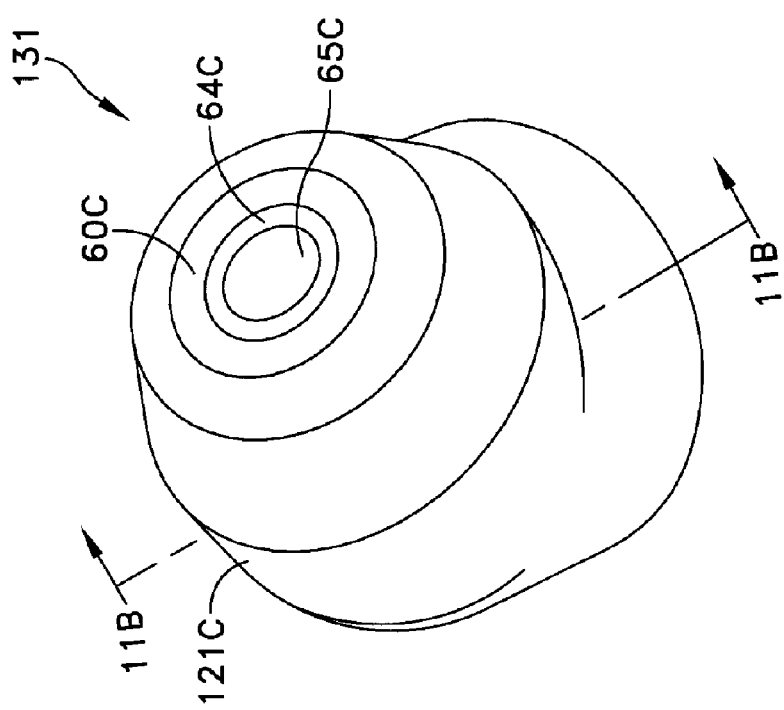
FIG. 11A is a perspective view of one embodiment of a probe tip with a patient compatible, compressible elastomeric outer layer that has a smaller diameter than the probe tip in FIG. 9A.

Each probe tip has certain common characteristics and distinguishing characteristics. Consequently FIGS. 9A and 9B describe one probe tip 100 in detail while the embodiment of FIGS. 10A and 10B and the embodiment in FIGS. 11A and 11B are described by highlighting the distinguishing characteristics. In the following discussion elements that are common to the structure shown in FIGS. 3 and 4 are used with suffix "A" in FIGS. 9A and 9B, "B" in FIGS. 10A and 10B and "C" in FIGS. 11A and 11B. Elements that are common to FIGS. 9A through 11B have corresponding suffices.

Referring now to FIGS. 9A and 9B, the probe tip 100 includes a central conductor 65A comprising a head 101 and a center conductor 102 that extends along a measurement axis 75A and terminates in line with a probe axis 54A. The head 101 terminates in a surface 103 that is coplanar with a measurement plane orthogonal to the measurement axis 75A.

An insulator 64A includes a cylindrical portion 104 having an outer surface 105 lying in the measurement plane. At the opposite end the insulator 64A terminates with an inwardly extending radial lip 106 that captures the head 101 and allows the passage of the center conductor 102.

The outer conductor 60A includes two pieces for facilitating manufacture. A first piece 107 includes a cylindrical wall 110 that terminates in a surface 111 at the measurement plane. At the other end an inwardly extending radial lip 112 captures the insulator 64A and provides a passage for the center conductor 102. The second piece 113 has a cylindrical wall 114 with internal threads 115 for being attached to threads, such as the threads on the threaded head portion 44 in FIGS. 3 and 4.

The opposite end of the second piece 113 is machined to define an oblique surface parallel to the measurement plane. Specifically, an oblique extension 116 from the cylindrical wall 114 terminates at an end surface 117 that carries the first piece 107. Similarly, a portion 120 of the wall 114 terminates at the end surface 117. The angle along which the end surface 117 extends determines the angular aspect between the measurement plane orthogonal to the axis 75A and the probe axis 54A. In this particular embodiment the aspect ratio is selected to be 45°.

In accordance with this invention, this structure is completed by overmolding a layer 121 that transitions to the measurement plane at a radius 122. The layer 121 can be molded of any of a number of patient-compatible, compressible elastomeric materials. Materials taken from a class of various elastomers such as silicone, polyurethane and polyvinyl with a hardness of less than 90 Shore A, will provide the benefits of this invention. A probe tip formed with an overmold of urethane with a hardness of about 35 Shore A has provided particularly good results.

As will be apparent from FIGS. 9A and 9B, as the probe tip 100 is inserted into a body cavity, such as an ear, the overmolded, soft, compressible material layer 121 will ease into the tissue. This process then minimizes tissue irritation. The overmolded layer 121 also isolates the outer conductor 60A electrically, as will be apparent to those skilled in the art.

FIGS. 10A and 10B depict a probe tip 130 that has the same basic construction as the probe tip 100 shown in FIGS. 9A and 9B. The difference is that the probe tip 130 establishes an angular aspect of 30°. In this particular embodiment, the outer conductor 60B, insulator 64B and center conductor 65B have the same construction as the corresponding elements shown in FIGS. 9A and 9B. Element 113B is modified so that the extension 117B has a greater length parallel to the axis 75B thereby to define a surface 117B that is orthogonal to the axis 75B. This also requires a machining modification of the portion 114B such that the surface 117B lies in an oblique plane relative to the probe axis 54B. The overmolded layer 121B has the same basic configuration as the overmolded layer 121 in FIGS. 9A and 9B modified only for purposes of accommodating the different configuration.

FIGS. 11A and 11B depict a probe tip 131 that again has a similar construction to the probe tip 100 in FIGS. 9A and 9B and has the same angular aspect. However the probe tip 131 has a smaller diameter. As before, except for dimensions, the outer conductor 60C, insulator 64C and center conductor 65C have the same basic construction as the corresponding elements shown in FIGS. 9A and 9B. In this embodiment the overmolded layer 121C has a conical surface 132 that extends back from a radius 122C. Tapering in this matter provides still further immunity from tissue irritation.

This invention has been disclosed in terms of certain embodiments. It will be apparent that many modifications can be made to the disclosed apparatus without departing from the invention. For example, different electro mechanical connections using alternate conductive members and mechanical connections, such as a signal connection could be substituted. Differently shaped tips, extensions and handles could be substituted. The overmolded portions in FIGS. 9A through 11B can also be modified by substituting different materials and that are patient compatible and compressible and by altering the specific shape in those figures. Therefore, it is the intent of the append claims to cover all such variations and modifications of the specifically disclosed embodiments as are covered by the claims.

What is claimed is:

1. In a dermal phase meter system including a data processing system and a probe, for providing input to the data processing system, said probe comprising:
   A) a set of probe tips, each probe tip including:
      i) an outer electrode with first connection means for attaching said probe tip to said probe along a probe tip connection axis,
      ii) a center electrode lying along a measurement axis perpendicular to a measurement surface defined by the outer and center electrodes, and
      iii) an insulating medium spacing said outer and center electrodes whereby the angle between said probe tip connection axis and said measurement axis for a given probe tip establishes an angular aspect between the probe axis and the measurement surface and different probe tips in said set establish different angular relationships, and
   B) probe tip support means for carrying a selected probe tip including a housing extending along the probe axis having:
      i) a first connection means at a proximal end thereof for connection to the data processing system,
      ii) a second connection means extending along the probe axis for engaging said probe outer electrode extending along the probe tip connection axis,
      iii) a third connection means in said housing proximate said second connection means and extending along the probe axis, said third connection means including an axially linearly displaceable, spring-biased, rigid conductor connected to said first connection means, each probe center electrode engaging and displacing said rigid conductor proximally as said probe tip is connected to said probe tip support means whereby said probe can operate with interchangeable probe tips that establish different angular aspects between said probe and measurement axes, and
   C) a patient compatible, compressible elastomeric layer about said outer electrode of at least one probe tip.

2. A probe as recited in claim 1 wherein said elastomeric layer comprises an elastorner exhibiting a hardness parameter in a range of less than 90 Shore A.

3. A probe as recited in claim 1 wherein said elastomeric layer is formed of a material taken from a class which includes silicone, polyurethane and polyvinyl.

4. A probe as recited in claim 1 wherein said elastomeric layer is formed of urethane.

* * * * *